United States Patent
Ikhlef

(10) Patent No.: US 10,531,848 B2
(45) Date of Patent: Jan. 14, 2020

(54) PACKAGING FOR CT DETECTOR

(71) Applicant: FMI Medical Systems Co., Ltd., Zhejiang (CN)

(72) Inventor: Abdelaziz Ikhlef, Hudson, OH (US)

(73) Assignee: FMI Medical Systems Co., Ltd., Zhejiang (CN)

( * ) Notice: Subject to any disclaimer, the term of this patent is extended or adjusted under 35 U.S.C. 154(b) by 106 days.

(21) Appl. No.: 15/980,938

(22) Filed: May 16, 2018

(65) Prior Publication Data

US 2019/0350545 A1    Nov. 21, 2019

(51) Int. Cl.
| | |
|---|---|
| *G01T 1/24* | (2006.01) |
| *A61B 6/00* | (2006.01) |
| *G01T 1/20* | (2006.01) |
| *A61B 6/03* | (2006.01) |

(52) U.S. Cl.
CPC ............ *A61B 6/4488* (2013.01); *A61B 6/032* (2013.01); *A61B 6/4233* (2013.01); *G01T 1/2018* (2013.01); *G01T 1/244* (2013.01)

(58) Field of Classification Search
CPC ..... A61B 6/032; A61B 6/4233; A61B 6/4488; G01T 1/2018; G01T 1/24; G01T 1/247
See application file for complete search history.

(56) References Cited

U.S. PATENT DOCUMENTS

| | | | |
|---|---|---|---|
| 3,532,159 A * | 10/1970 | Broadwell .......... | F28D 15/0233 165/104.22 |
| 7,233,640 B2 | 6/2007 | Ikhlef et al. | |
| 2006/0289765 A1* | 12/2006 | Ikhlef .................. | G01T 1/2018 250/341.5 |
| 2007/0086565 A1 | 4/2007 | Thompson et al. | |
| 2010/0021378 A1* | 1/2010 | Rousso ................. | A61B 5/411 424/1.11 |
| 2011/0211667 A1 | 9/2011 | Ikhlef et al. | |
| 2012/0014502 A1 | 1/2012 | De Man et al. | |

* cited by examiner

*Primary Examiner* — David P Porta
*Assistant Examiner* — Fani Boosalis
(74) *Attorney, Agent, or Firm* — Fishman Stewart PLLC

(57) ABSTRACT

A detector assembly for a CT system includes a plurality of detector modules, each detector module including a grid of pixelated scintillators, a photodiode having pixelations that correspond with the pixelated scintillators, and an electronics package for processing acquired X-ray data, a support structure extending along a Z-direction of the CT system and having the plurality of detector modules positioned thereon, and a heat sink extending along the Z-direction and having the support structure mounted thereon, the heat sink including a passageway passing therethrough and along the Z-direction, such that cooling air may pass into the passageway at a first end of the heat sink and exit the passageway at a second end of the heat sink opposite the first end.

20 Claims, 8 Drawing Sheets

PACKAGING FOR CT DETECTOR

TECHNICAL FIELD

This disclosure relates generally to diagnostic imaging and, more particularly, to an apparatus and method of fabricating packaging of a detector for a computed tomography (CT) system.

BACKGROUND

Typically, in computed tomography (CT) imaging systems, a rotatable gantry includes an x-ray tube, detector, data acquisition system (DAS), and other components that rotate about a patient table that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into visible light photons within the scintillator, and then to electrical signals within the photodiode. The electrical signals are digitized and then received and processed within the DAS. The processed signals are transmitted via a slipring (from the rotational side to the stationary side) to a computer for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector.

Third generation multi-slices CT scanners typically include detectors having scintillator/photodiodes arrays. These detectors are positioned in an arc where the focal spot is the center of the corresponding circle. These detectors generally have scintillation crystal/photodiode arrays, where the scintillation crystal absorbs x-rays and converts the absorbed energy into visible light. A photodiode is used to convert the light to an electric current. The reading is typically linear to the total energy absorbed in the scintillator.

Typically, CT systems obtain raw data and then reconstruct images using various known pre-processing and post-processing steps to generate a final reconstructed image. That is, CT systems may be calibrated to account for x-ray source spectral properties, detector response, and other features, to include temperature. Raw x-ray data are pre-processed using known steps that include offset correction, reference normalization, and air calibration steps, as examples.

In recent years, the development of volumetric or cone-beam CT technology has led to an increase in the number of slices used in CT detectors for computed tomography systems. The detector technology used in large coverage CT enables greater coverage in patient scanning by increasing the area exposed, by using back-illuminated photodiodes. The increase of the number of slices results in an increase in the width of the detector in Z-axis (e.g., along the patient length). Because it is impractical to build very large modules in monolithic structure to cover 160 mm or more in the Z-axis, due to manufacturing cost and reliability concerns, in one example stack smaller modules (mini-modules) are built along the Z-axis.

However, image quality in a CT canner is dependent on several components in the system such as the detector, the x-ray tube and high voltage generator, the system and component geometry, and the thermal management, etc. In third generation CT scanners, the detector for example, typically has very strict specifications to ensure good image quality and some of these requirements include but are not limited to: a) stability of the detector over time and temperature, b) focal spot drift, c) stable and high light output over the lifetime of the detector, etc.

One important factor is related to thermal management. Typically, detectors are calibrated at a known temperature and imaging data is obtained. However, a variety of factors can cause the detectors to fall out of calibration. For instance, temperature within the room or suite (in which the CT scanner is placed) can vary or drift throughout the day, or power dissipation within the CT scanner can cause temperature changes depending on how heavy the scanner is used. In fact, there are numerous factors that can lead to variation in detector temperatures, which can lead to the detector falling out of calibration.

And, the components within the detector itself can be sensitive to temperature, and the gain of the detector components may decrease with increased temperature. To counter this sensitivity, in one example it is known that detectors or detector assemblies may be heated during calibration and use to ensure a stable temperature during operation. However, heating the detector components may have the deleterious or counter effect of reducing overall dose efficiency, given that the gain may be reduced. Thus, on one hand stable operation and extended periods of operation may be achieved by heating the detectors or detector assemblies. However, such heating may come at the cost of dose efficiency. Further, as detector assemblies have grown along the Z-axis in recent years, the task of thermal management may be more difficult as components within the detector may be prone to thermal drift.

Thus, there is a need to improve thermal management within a CT detector or CT detector module.

BRIEF DESCRIPTION

Embodiments are directed toward an apparatus and method of fabricating a spherical CT detector.

A detector assembly for a CT system includes a plurality of detector modules, each detector module including a grid of pixelated scintillators, a photodiode having pixelations that correspond with the pixelated scintillators, and an electronics package for processing acquired X-ray data, a support structure extending along a Z-direction of the CT system and having the plurality of detector modules positioned thereon, and a heat sink extending along the Z-direction and having the support structure mounted thereon, the heat sink including a passageway passing therethrough and along the Z-direction, such that cooling air may pass into the passageway at a first end of the heat sink and exit the passageway at a second end of the heat sink opposite the first end.

A method of assembling a detector assembly for a CT system includes providing a plurality of detector modules, each detector module including a grid of pixelated scintillators, a photodiode having pixelations that correspond with the pixelated scintillators, and an electronics package for processing acquired X-ray data, providing a support structure that extends along a Z-direction of the CT system, positioning the plurality of detector modules on the support structure, providing a heat sink that extends along the Z-direction, the heat sink including a passageway passing therethrough and along the Z-direction, such that cooling air may pass into the passageway at a first end of the heat sink and exit the passageway at a second end of the heat sink opposite the first end, and mounting the support structure to the heat sink.

A CT system includes a rotatable gantry having an opening for receiving an object to be scanned, an x-ray tube having a focal spot from which x-rays emit, and a detector assembly comprising one or more scintillator modules for receiving x-rays from the focal spot. The detector assembly includes a plurality of detector modules, each detector module including a grid of pixelated scintillators, a photodiode having pixelations that correspond with the pixelated scintillators, and an electronics package for processing acquired X-ray data, a support structure extending along a Z-direction of the CT system and having the plurality of detector modules positioned thereon, and a heat sink extending along the Z-direction and having the support structure mounted thereon, the heat sink including a passageway passing therethrough and along the Z-direction, such that cooling air may pass into the passageway at a first end of the heat sink and exit the passageway at a second end of the heat sink opposite the first end.

Various other features and advantages will be made apparent from the following detailed description and the drawings.

DETAILED DESCRIPTION

The operating environment of disclosed embodiments is described with respect to a sixteen-slice computed tomography (CT) system. Embodiments are described with respect to a "third generation" CT scanner, however it is contemplated that the disclosed embodiments are applicable to other imaging systems as well, and for CT systems having more or less than the illustrated sixteen-slice system.

Figure 1:
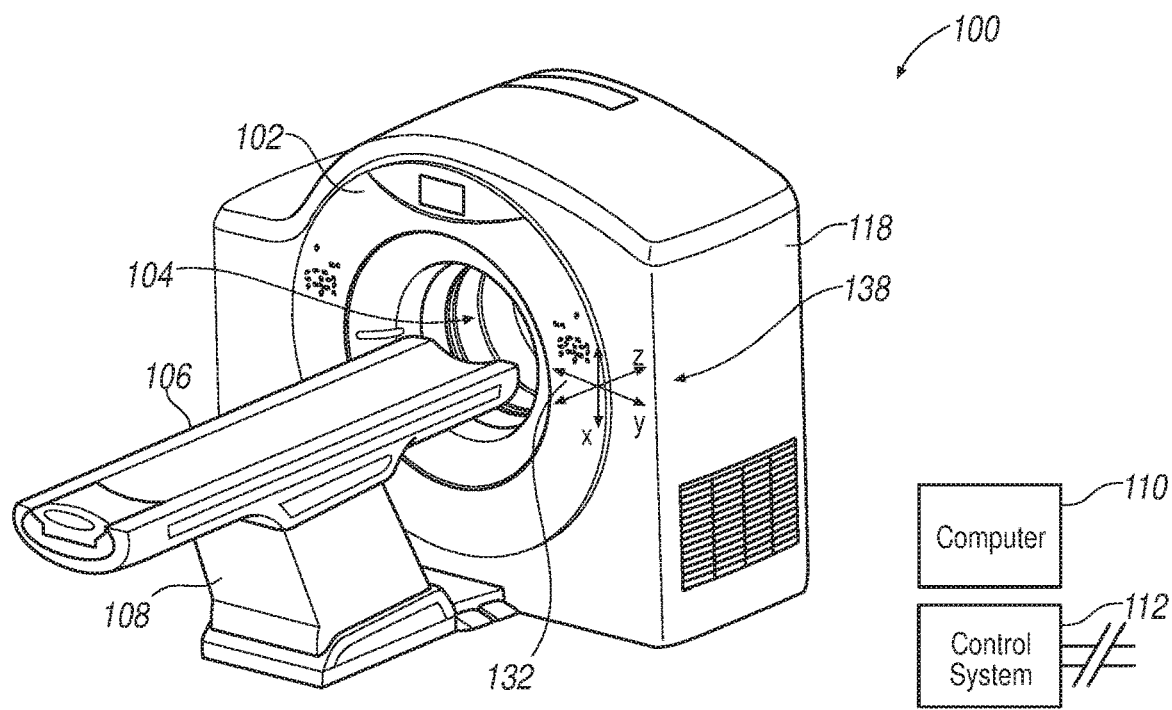
FIG. 1 is a perspective view of a CT imaging system.
Figure 2:
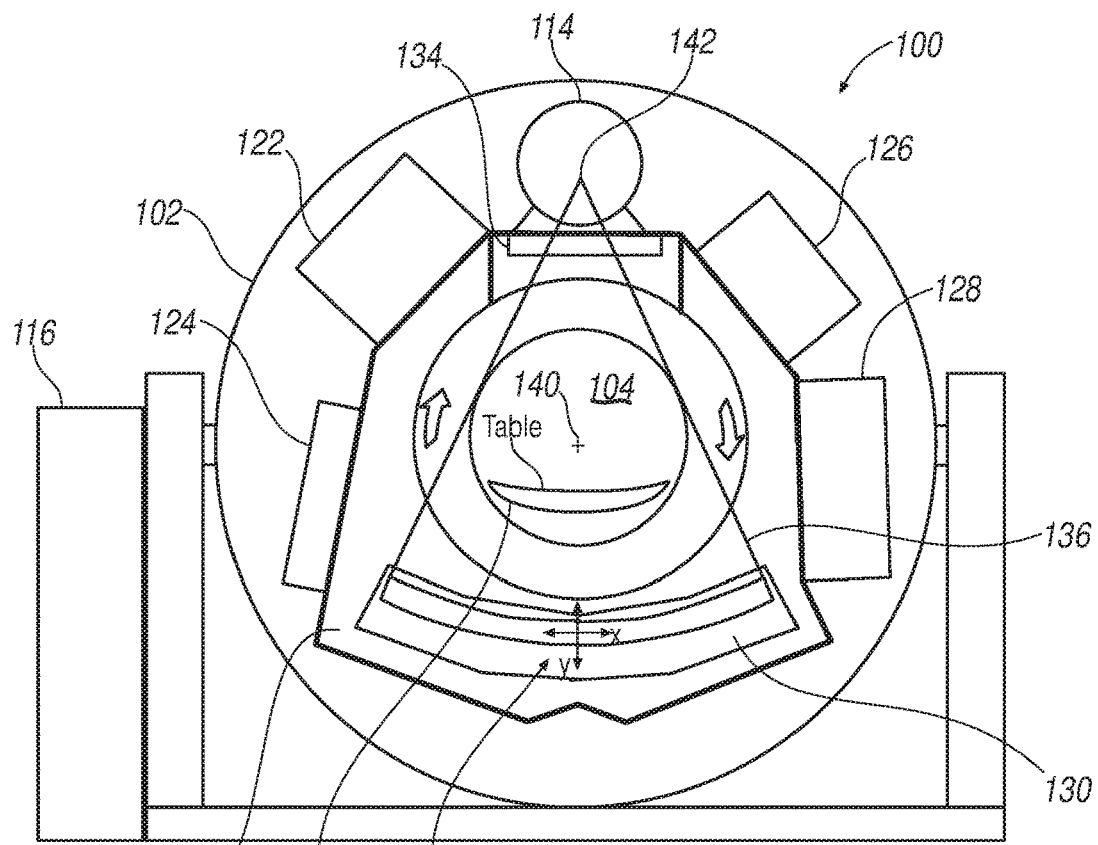
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction algorithms, or an image reconstructor may be provided as a separate processing unit. Control system 112 provides control commands for operating gantry 102, an x-ray tube 114, and a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a generator 128, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is caused to rotate about the patient up to typically a few Hz in rotational speed, and table 106 is caused to move the patient axially within opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals that are digitized and passed to DAS 124, and then to computer 110 where the data is further processed to generate an image. The imaging data may be stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and a gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
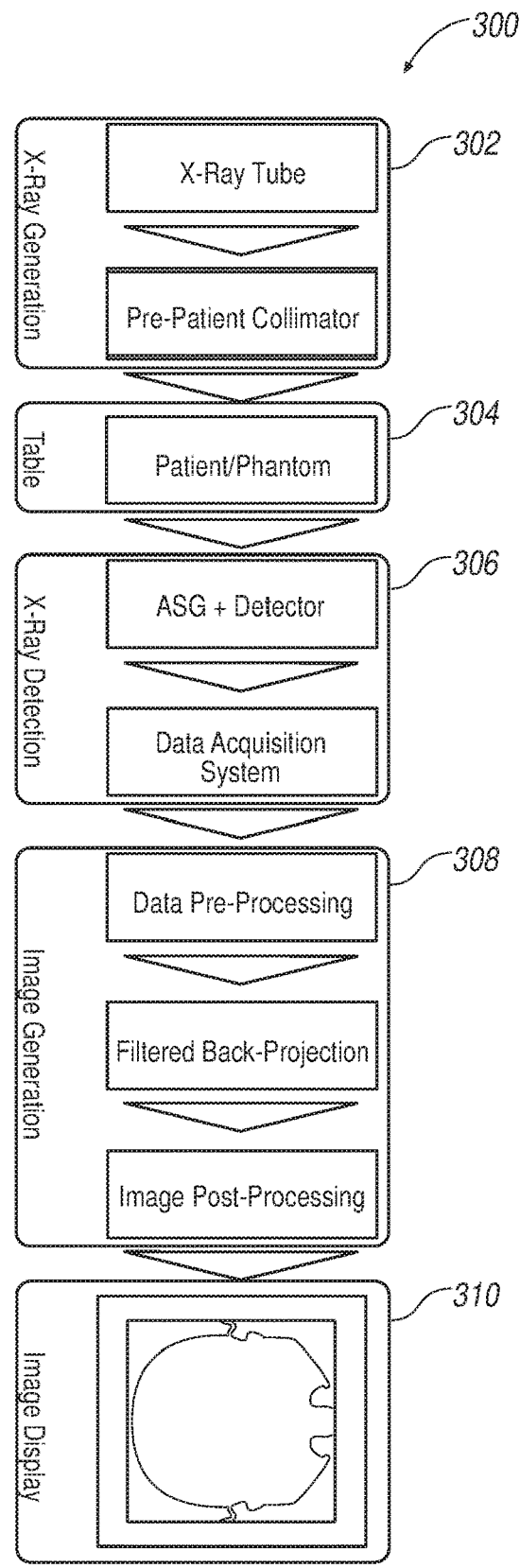
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which time table 106 passes 304 through opening 104 of gantry 102. In one example table 106 may have a patient thereon, and in another example a phantom may be used for calibration purposes.

X-ray detection 306 occurs when x-rays having emitted from x-ray tube 114 pass to detector assembly 130. An anti-scatter grid (ASG) prevents x-ray scatter (emitting for example from the patient as secondary x-rays and in a direction that is oblique to x-ray beam 136), by generally passing x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slipring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
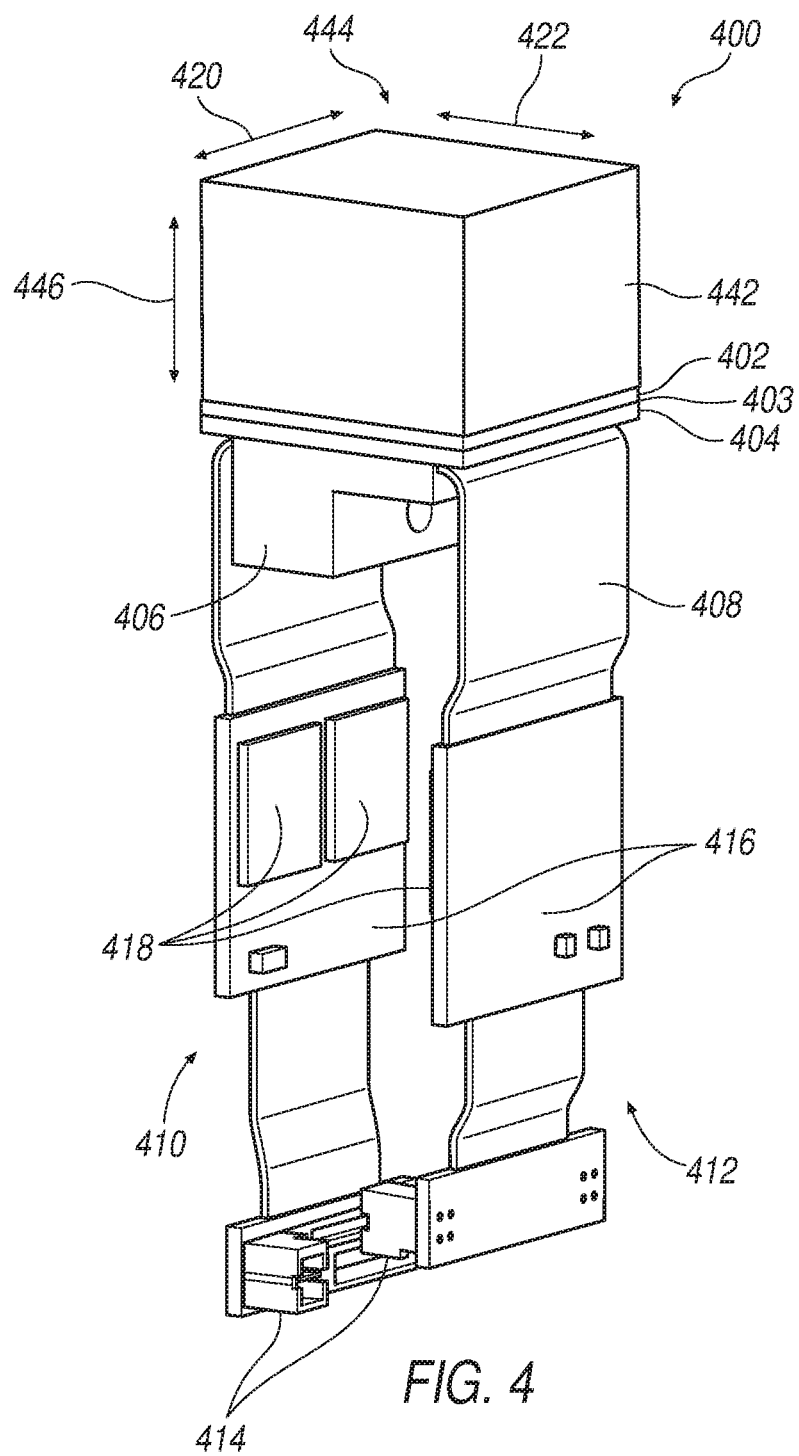
FIG. 4 illustrates a module or mini-module having a collimator attached thereto.

FIG. 4 illustrates a module or mini-module 400 having been assembled according to the disclosure. Module 400 includes a grid of pixelated scintillators or scintillating array 402 positioned on a substrate 404, having a photodiode 403 therebetween. An alignment block or support structure 406 mechanically supports module 400. Positioned between support structure 406 and substrate 404 is a flex circuit 408, which wraps within module 400 and includes a first end 410 and a second end 412. Each end 410, 412 includes electrical connectors 414, a circuit board or electronics package 416, ASIC or processors 418, and other associated electronic components (not shown). Module 400, when placed on a gantry of a CT system, such as system 100 above, has an orientation of a Z or slice direction 420 and an X or channel direction 422.

An anti-scatter grid 442 having a plurality of plates 444 is positioned on an upper surface of scintillating array 402. In the example shown, anti-scatter grid 442 is a monolithic device having plates that extend in X or channel direction 422. Anti-scatter grid 442 in the illustrated example may be fabricated using a plurality of tungsten plates, or as another example may be fabricated using 3D printing technology and having high density materials such as tungsten or other x-ray absorbing materials therein. Accordingly, in one example, anti-scatter grid 442 is a two-dimensional (2D) collimator with plates 444 spaced from one another having a spacing that corresponds with a spacing of pixels.

Plates 444 may thereby be fabricated in anti-scatter grid 442 to be slightly non-parallel to one another so that each may be directed and approximately aimed toward a focal spot of a CT system. For instance, referring to FIG. 2, modules 400 may be positioned accordingly within CT detector assembly 130 and on gantry 102, having each plate 444 extending along a length and in a direction 446 such that, when CT detector 130 is positioned in CT system 100, the length of plates 444 extend 446 approximately toward focal spot 142 of CT system 100.

Figure 5:
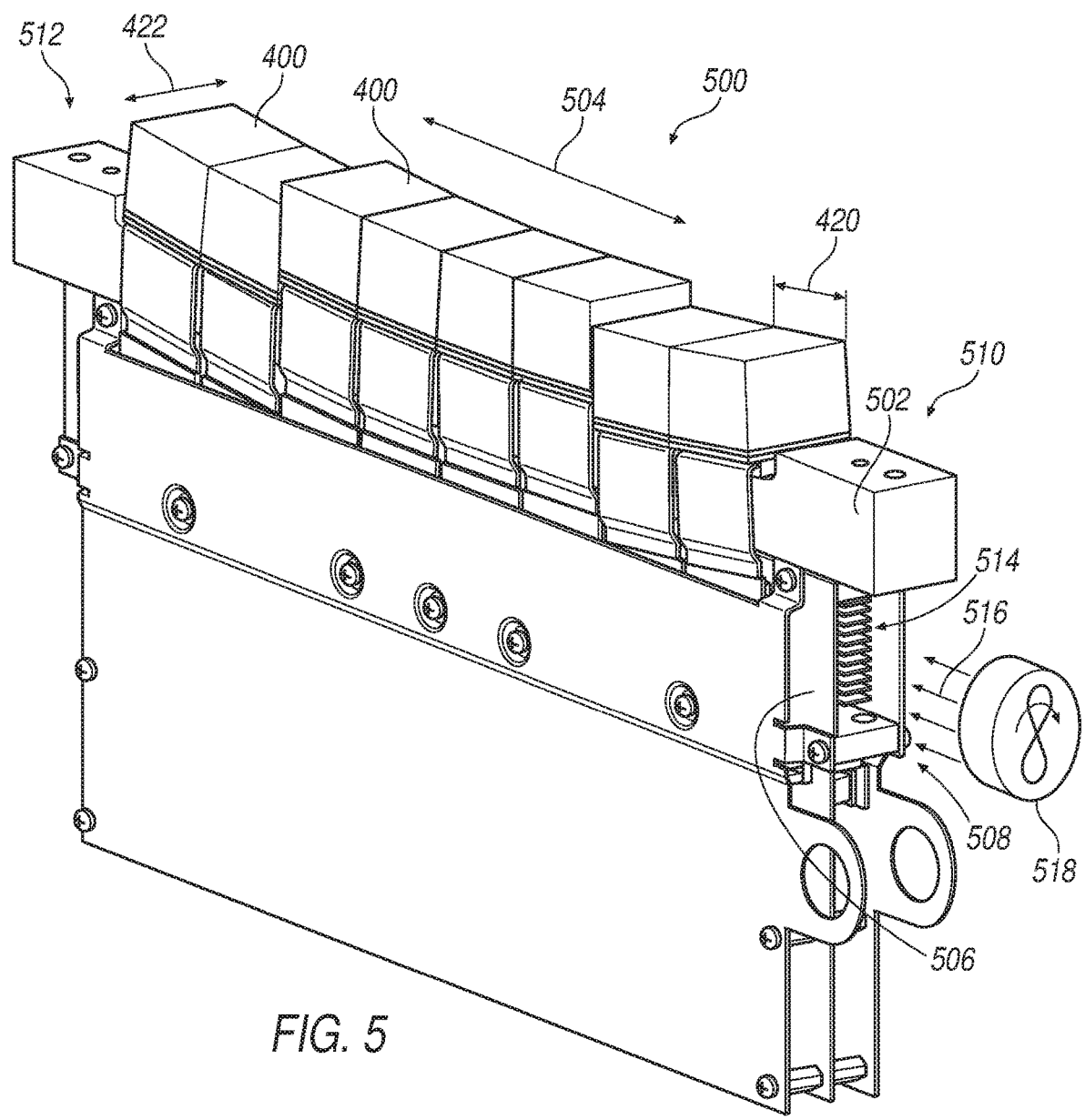
FIG. 5 a detector sub-assembly having a plurality of modules.

Referring now to FIG. 5, a detector sub-assembly 500 shows a plurality of modules 400, being positioned on an alignment block 502. As shown, each module 400 includes Z or slice direction 420, which combine to provide a composite coverage in a system Z direction 504, which corresponds with triad 138 in FIGS. 1 and 2. Correspondingly, each module 400 includes X or channel direction 422, and modules 400 are thereby combined or stacked side-by-side to form a plurality of detectors, corresponding with triad 138 of FIGS. 1 and 2, forming detector assembly 130. Thus, according to the disclosure, each module 400 is fabricated in the fashion described herein. As such, global system tolerances do not accumulate, such as if all plates 444 were placed with respect to alignment block 502, for example. In addition, each module 400 may be classified and placed within the detector according to the measured quality of the modules.

Referring now to FIG. 5, a detector assembly or sub-assembly 500 shows a plurality of modules 400, being positioned on an alignment block 502. As shown, each module 400 includes Z or slice direction 420, which combine to provide a composite coverage in a system Z direction 504, which corresponds with triad 138 in FIGS. 1 and 2. Correspondingly, each module 400 includes X or channel direction 422, and modules 400 are thereby combined or stacked side-by-side to form a plurality of detectors, corresponding with triad 138 of FIGS. 1 and 2, forming detector assembly 130.

Thus, according to the disclosure, a detector assembly 500 for CT system 100 includes plurality of detector modules 400, each detector module including a grid of pixelated scintillators 402, a reflector (as is commonly known), a photodiode 403 having pixelations that correspond with the pixelated scintillators 402, and an electronics package 416 for processing acquired X-ray data. A support structure 502, corresponding with support structure 406 above, extends along Z-direction 504 of CT system 100 and includes plurality of detector modules 400 positioned thereon. A heat sink 506 extends along Z-direction 504 and includes support structure 502 mounted thereon. Heat sink 504 includes a passageway 508 passing therethrough and along Z-direction 504, such that cooling air may pass into passageway 508 at a first end 510 of heat sink 506 and exit passageway 508 at a second end 512 of heat sink 506 opposite first end 510. Heat sink 506 includes a plurality of fins or plates 514 positioned within passageway 508 and are thermally coupled to heat sink 506, each of plurality of plates 508 extending along Z-direction 504. As such, air or another cooling medium 516 is blown into passageway 508 via a fan, as an example, represented by element 518 in FIG. 5.

Figure 9:
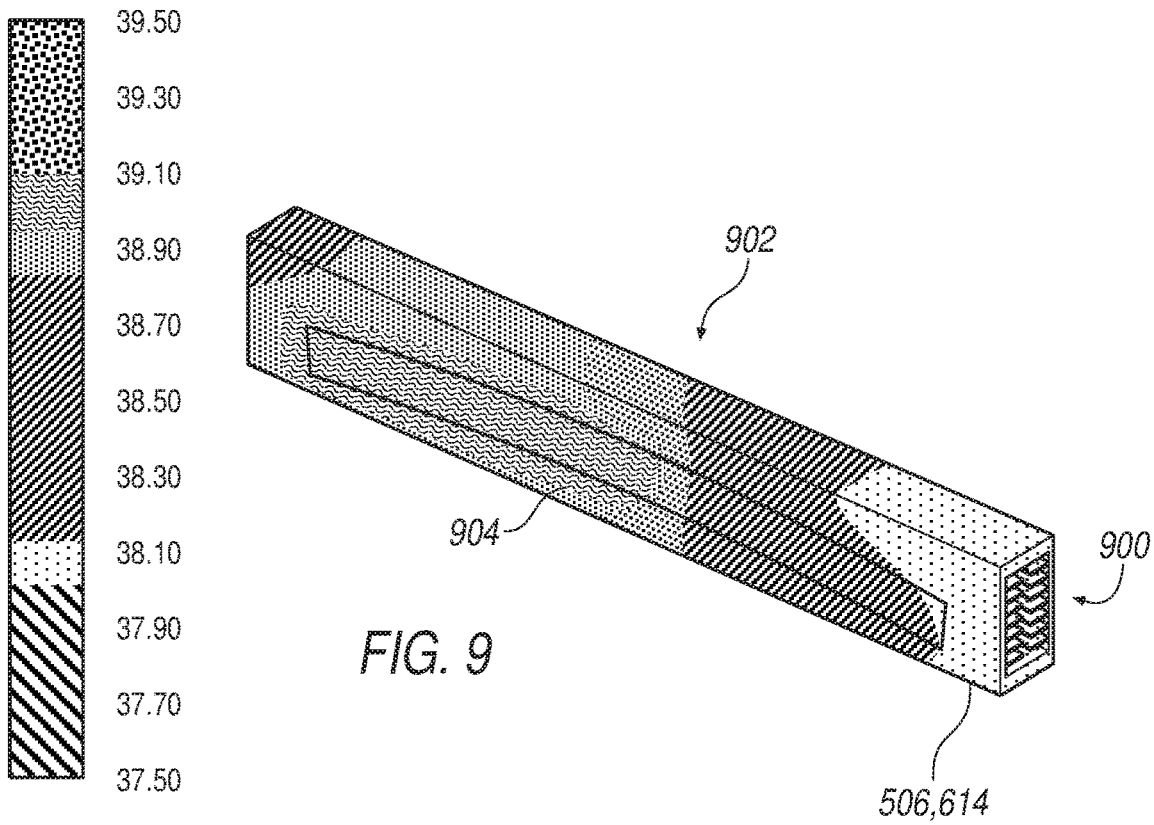
FIG. 9 shows temperature distribution of the heat sink of FIG. 7A.

Referring to FIG. 9, an exploded and perspective view 600 of detector assembly 500 is shown. Modules, or mini-modules 400 are shown proximate one another, and proximate support structure 502. Support structure 502 includes surfaces 602, 604, 606 which include steps 608. And, surfaces 602, 604, 606 may themselves include non-parallel surfaces such that each individual mini-module 400 may be directly aimed toward focal spot 142, regardless of which step it is positioned on.

Also, according to the disclosure detector assembly 500 includes a heater 610 and a thermal barrier 612. Detector assembly 500 includes a heat sink 614, a FPGA printed circuit board 616, and support plates 618. As known in the art, thermal control is an important aspect of detector design, and thus heater 610 uniformly heats support structure 502, thereby maintaining each of mini-modules 400 at uniform temperature during calibration and use. Thermal barrier 612 reduces the propensity for heat to flow from ASIC or processors 418 on each of circuit board or electronics package 416. Heat sink 614 is thermally coupled to each circuit board or electronics package 416, preventing heat from flowing to support structure 502 to negatively affect thermal calibration or performance of the detectors.

Figure 6:
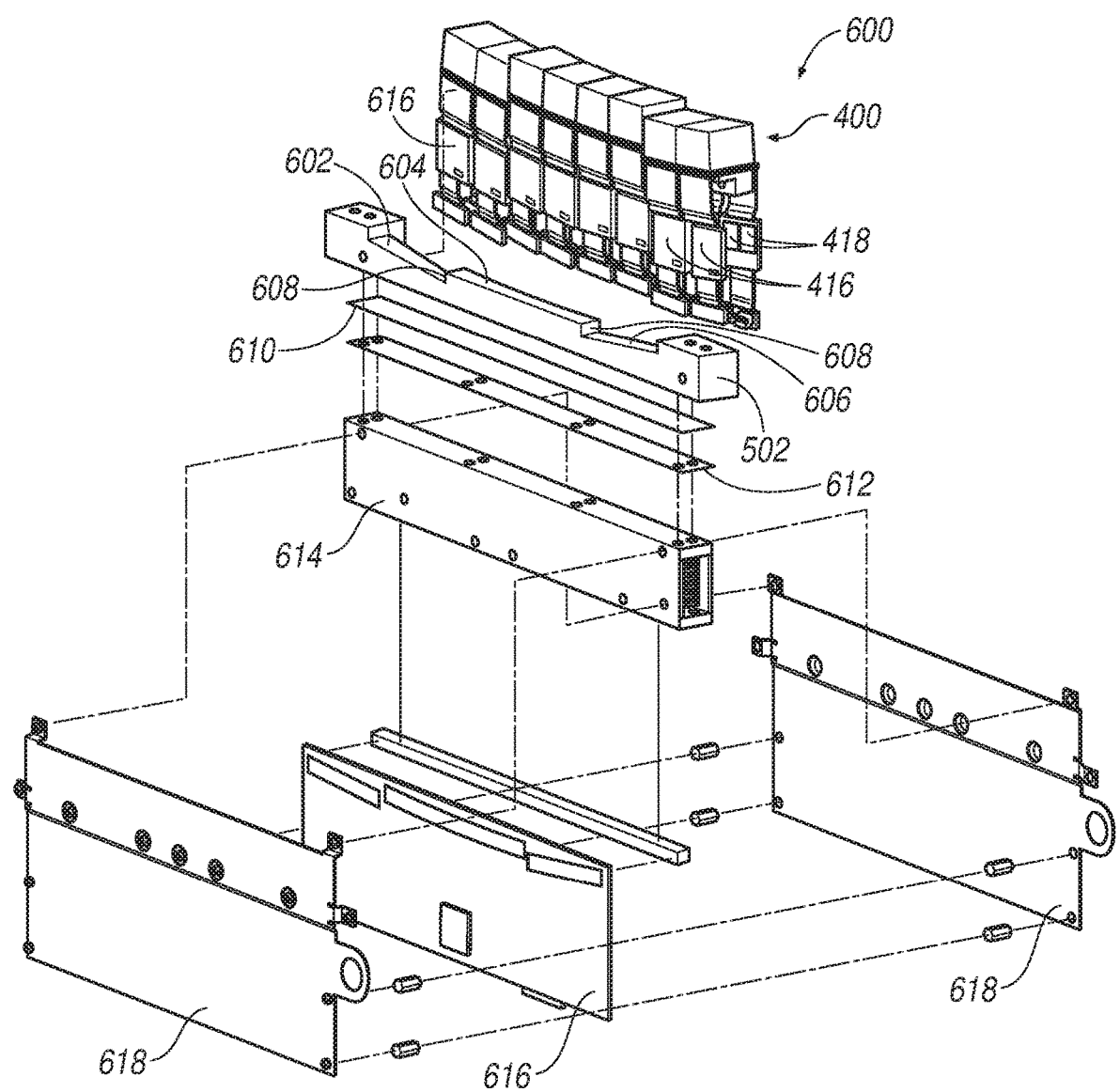
FIG. 6 illustrates an exploded and perspective view that includes the detector sub-assembly of FIG. 5.
Figure 7A:
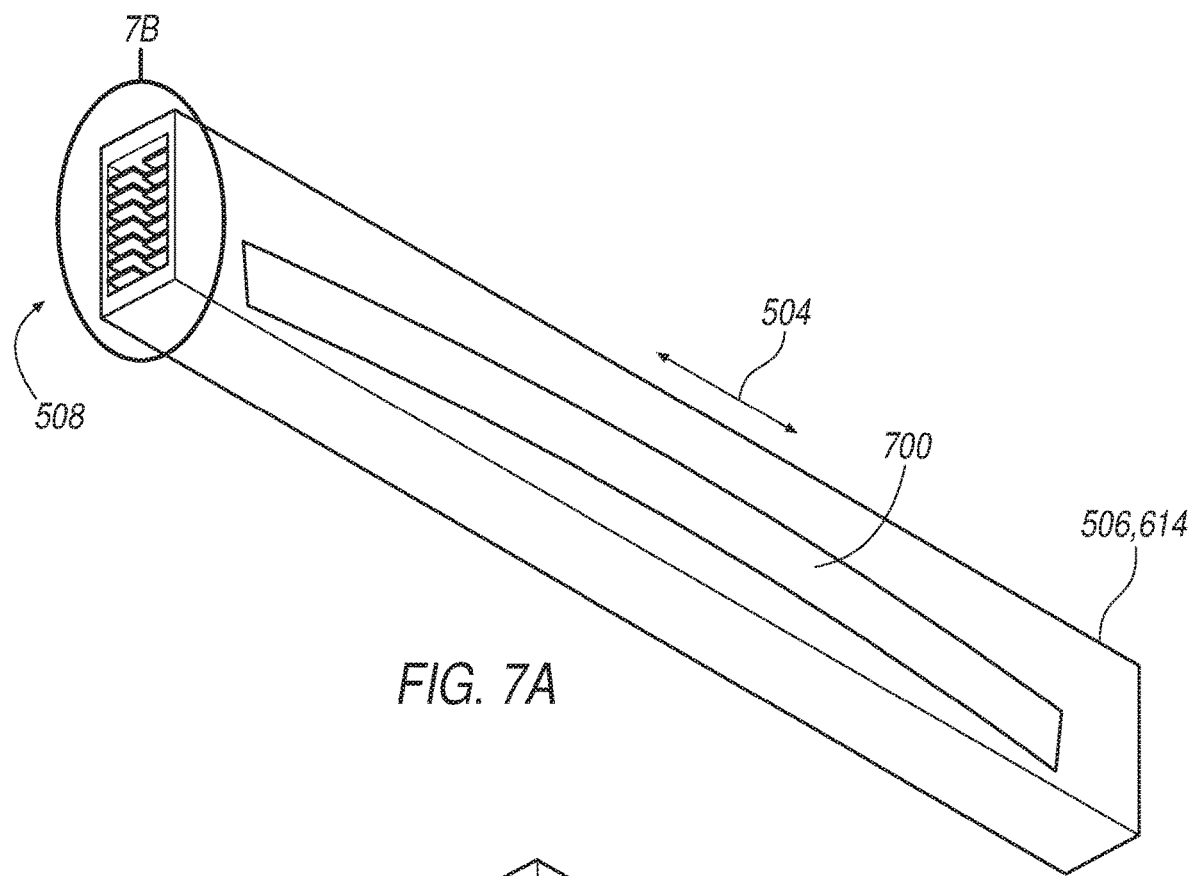
FIG. 7A shows a heat sink according to one example.

Referring to FIG. 7A, heat sink 506, 614 is shown, including an area 700 that represents (for temperature illustration purposes), an area in which heat sources from ASICs or processors 418 are located. That is, referring to FIGS. 4, 5, and 6, electronics packages 416 include ASIC or processors 418, and electronics packages 416 are thermally coupled to heat sink 506, 614 such that heat is input to heat sink 506, 614 approximately along area 700. As seen in corresponding FIG. 7B, plates 514 are positioned within passageway 508 and thermally coupled to heat sink 506, 614, each of plates 514 extending along Z-direction 504.

Figure 8A:
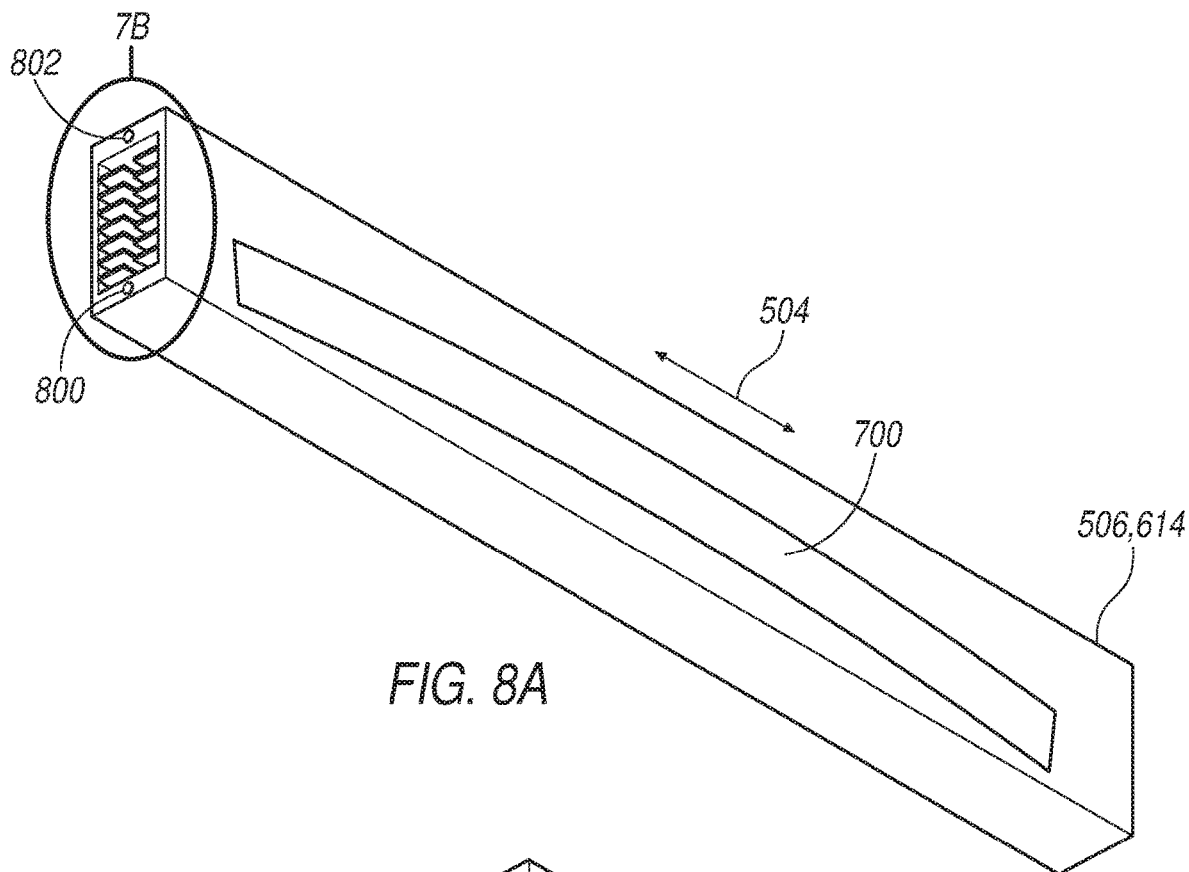
FIG. 8A shows a heat sink according to one example, having heat transfer enhancement devices therein.
Figure 8B:
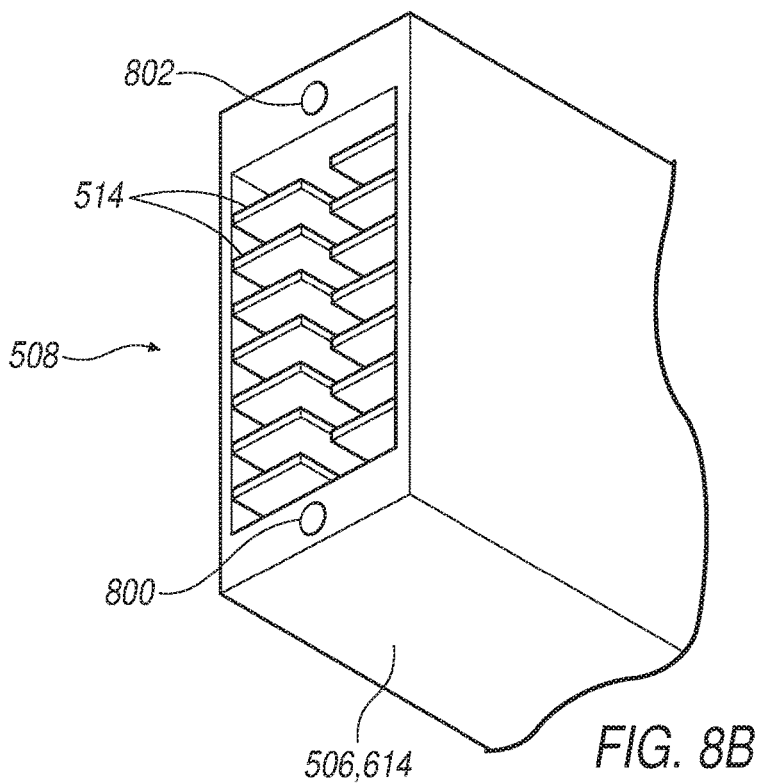
FIG. 8B shows an end view of the heat sink of FIG. 8A.

Referring to FIGS. 8A and 8B, heat sink 506, 614 is shown, including area 700 that represents the area in which heat sources from ASICs or processors 418 are located. As seen in corresponding FIG. 8B, plates 514 are positioned within passageway 508 and thermally coupled to heat sink 506, 614, each of plates 514 extending along Z-direction 504. However, in this example, heat transfer enhancement devices 800, 802 may be included such as heat pipes that are positioned within heat sink 506, 614 and extending along Z-direction 504. Heat pipes 800, 802, as known in the art, are heat-transfer devices that combine the principles of both thermal conductivity and phase transition to effectively transfer heat between two solid interfaces. At a hot interface of a heat pipe a liquid in contact with a thermally conductive solid surface turns into a vapor by absorbing heat from that surface. The vapor then travels along the heat pipe to the cold interface and condenses back into a liquid—releasing the latent heat of vaporization. The liquid then returns to the hot interface through either capillary action, centrifugal force, or gravity, and the cycle repeats. Due to the very high heat transfer coefficients for boiling and condensation, heat pipes 800, 802 are therefore highly effective thermal conductors, reducing the temperature gradient along heat sink 506, 614. According to one example, instead of using heat pipes 800, 802, copper may be used, although copper typically includes a conduction coefficient that may be below that provided by heat pipes.

Figure 7B:
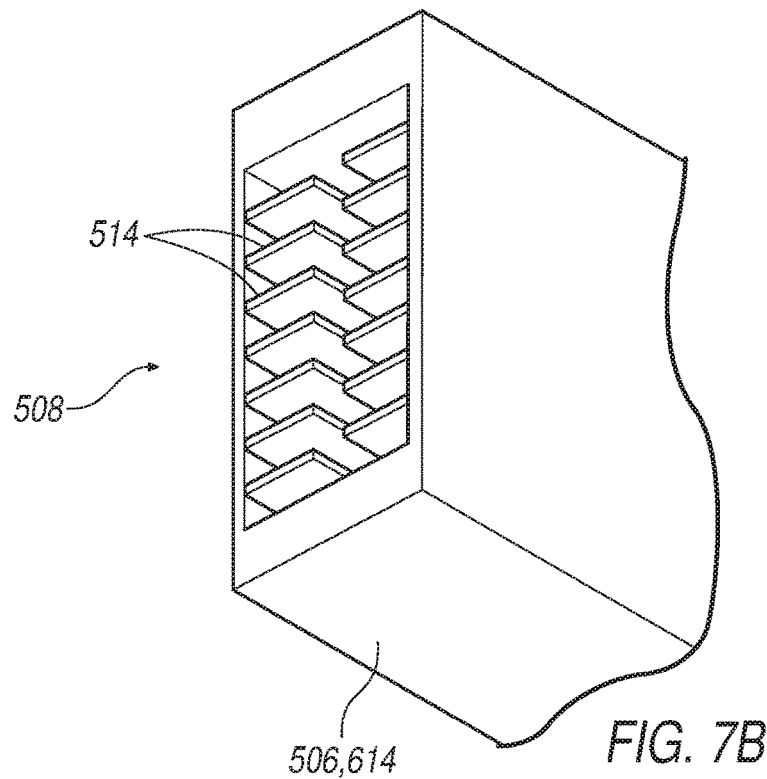
FIG. 7B shows an end view of the heat sink of FIG. 7A.
Figure 10:
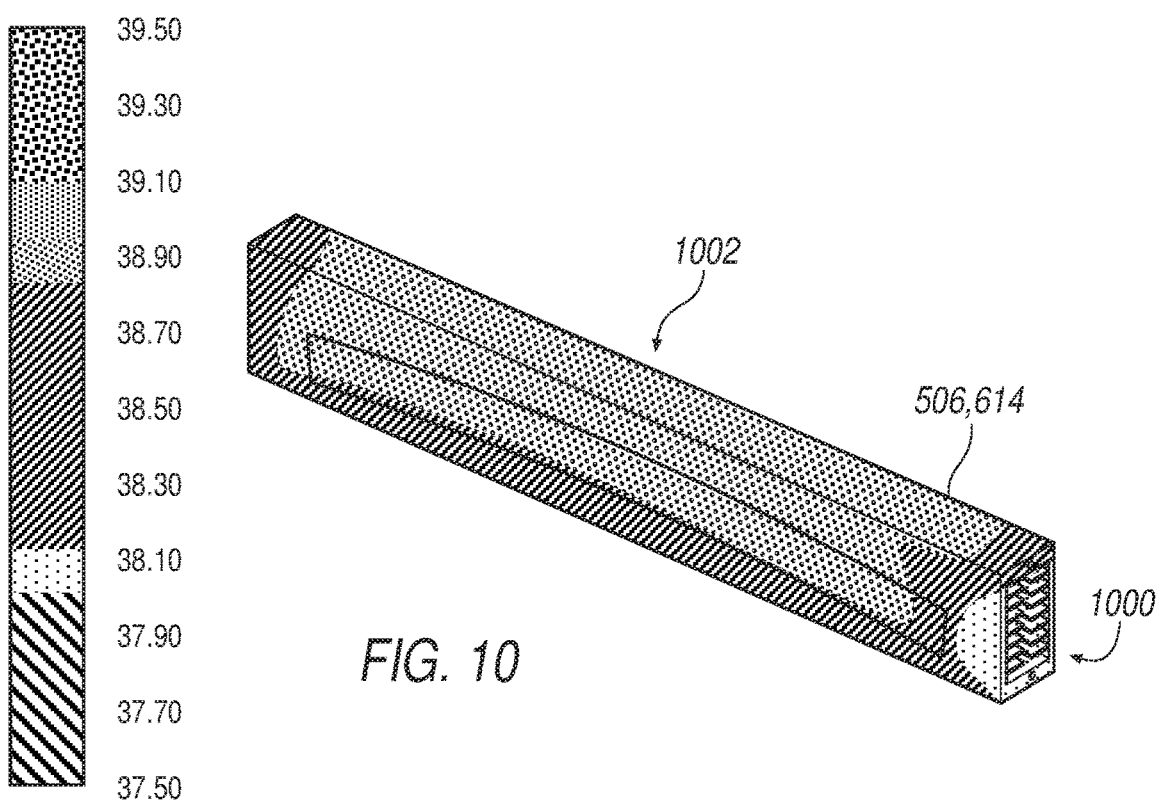
FIG. 10 shows temperature distribution of the heat sink of FIG. 8A.

Referring to FIGS. 9 and 10, exemplary thermal results are shown for heat sink 506, 614. FIG. 9 shows exemplary results for heat sink 506, 614 corresponding to FIGS. 7A and 7B, and FIG. 10 shows exemplary results for heat sink 506, 614 corresponding to FIGS. 8A and 8B. As can be seen, inlet air 900 results in relatively cool temperatures in heat sink 506, 614. However, in the example with no heat sink 902, a hot region 904 results. On the other hand, inlet air 1000 likewise results in relatively cool temperatures in heat sink 506, 614. However, in the example with a heat sink 1002, temperature distribution along a length of heat sink 506, 614 is much more uniform.

Thus, the disclosed architecture includes an accurate process in stacking and classification of mini-modules, with a precise mechanical packaging which enables precise alignment, removability and reparability.

In the disclosed example, mini-module elements include 32×32 arrays to achieve 256 or more slices by stacking them in a curved Z-axis. Mini-modules use four analog-to-digital converter ASICs, with 256 channels each. Thus, in in this example, the total number of ASICs in the full detector will be 1120 ASICs or 286720 channels. According to the disclosure, the ASICs are cooled to maintain proper functionalities, as they are located inside the detector. In one example, air is passed into the heat sinks, cooling the heat sinks by convection.

As indicated, the disclosed subject matter may be with or without heat pipes. In the disclosed design both X-axis and Z-axis are curved to form a sphere where the focal spot is the center of the sphere. In a 256 slice detector, the length of a module may reach more than 256 mm. Because air flows from one end to the other, air pressure and temperature variation may lead temperature drift from one end to the other. Thus, the packaging of the module and the heat sink is designed such that there is enough air and minimized pressure drop.

In addition to the heat-sink design, the thermal insulation between the heat sources (ASICs) and the photodiodes/ASG are achieved by inserting a thermal barrier. In this design, the photodiode and ASG are thermally controlled actively by a heater and the heat from the heater is insulated from the heat sink. The heat from the ASICs is removed by air convection in the heat sinks.

As such, according to the disclosure, a simplified packaging using conventional thermal management is disclosed. Uniform temperature distribution is achieved along the Z-axis, removing temperature gradient issues. Thus, gain drift is minimized from calibration to scanning and between modules by achieving pseudo-isothermal modules. Sensitivity to thermal drift is minimized because of accurate alignment to the scintillation array kerfs. The thermal packaging is optimized by achieving thermal separation between heat sink and heating elements.

Other impacts of the disclosed subject matter on products such as CT scanner include but are not limited to, better and stable image quality through large range of room temperatures, cost and reliability improvement by using conventional thermal solutions, and local control of the thermal status of each module independently leading to more accurate testability and operation.

Thus, a detector assembly for a CT system includes a plurality of detector modules, each detector module including a grid of pixelated scintillators, a reflector, a photodiode having pixelations that correspond with the pixelated scintillators, and an electronics package for processing acquired X-ray data, a support structure extending along a Z-direction of the CT system and having the plurality of detector modules positioned thereon, and a heat sink extending along the Z-direction and having the support structure mounted thereon, the heat sink including a passageway passing therethrough and along the Z-direction, such that cooling air may pass into the passageway at a first end of the heat sink and exit the passageway at a second end of the heat sink opposite the first end.

A method of assembling a detector assembly for a CT system includes providing a plurality of detector modules, each detector module including a grid of pixelated scintillators, a reflector, a photodiode having pixelations that correspond with the pixelated scintillators, and an electronics package for processing acquired X-ray data, providing a support structure that extends along a Z-direction of the CT system, positioning the plurality of detector modules on the support structure, providing a heat sink that extends along the Z-direction, the heat sink including a passageway passing therethrough and along the Z-direction, such that cooling air may pass into the passageway at a first end of the heat sink and exit the passageway at a second end of the heat sink opposite the first end, and mounting the support structure to the heat sink.

A CT system includes a rotatable gantry having an opening for receiving an object to be scanned, an x-ray tube having a focal spot from which x-rays emit, and a detector assembly comprising one or more scintillator modules for receiving x-rays from the focal spot. The detector assembly includes a plurality of detector modules, each detector module including a grid of pixelated scintillators, a reflector, a photodiode having pixelations that correspond with the pixelated scintillators, and an electronics package for processing acquired X-ray data, a support structure extending along a Z-direction of the CT system and having the plurality of detector modules positioned thereon, and a heat sink extending along the Z-direction and having the support structure mounted thereon, the heat sink including a passageway passing therethrough and along the Z-direction, such that cooling air may pass into the passageway at a first end of the heat sink and exit the passageway at a second end of the heat sink opposite the first end.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A detector assembly for a CT system, comprising:
a plurality of detector modules, each detector module including a grid of pixelated scintillators, a photodiode having pixelations that correspond with the pixelated scintillators, and an electronics package for processing acquired X-ray data;
a support structure extending along a Z-direction of the CT system and having the plurality of detector modules positioned thereon; and
a heat sink extending along the Z-direction and having the support structure mounted thereon, the heat sink including a passageway passing therethrough and along the Z-direction, such that cooling air may pass into the passageway at a first end of the heat sink and exit the passageway at a second end of the heat sink opposite the first end.

2. The detector assembly of claim 1, further comprising a plurality of plates positioned within the passageway and thermally coupled to the heat sink, each of the plurality of plates extending along the Z-direction.

3. The detector assembly of claim 1, further comprising a heat transfer enhancement device positioned within the heat sink and extending along the Z-direction.

4. The detector assembly of claim 3, wherein the heat transfer enhancement device is a heat pipe having a convective heat transfer medium positioned therein.

5. The detector assembly of claim 3, wherein the heat transfer enhancement device is a copper pipe.

6. The detector assembly of claim 1, further comprising a heater positioned between the support structure and the heat sink.

7. The detector assembly of claim 6, further comprising a thermal barrier positioned between the heat sink and the heater.

8. A method of assembling a detector assembly for a CT system, the method comprising:
providing a plurality of detector modules, each detector module including a grid of pixelated scintillators, a photodiode having pixelations that correspond with the pixelated scintillators, and an electronics package for processing acquired X-ray data;
providing a support structure that extends along a Z-direction of the CT system;
positioning the plurality of detector modules on the support structure;
providing a heat sink that extends along the Z-direction, the heat sink including a passageway passing therethrough and along the Z-direction, such that cooling air may pass into the passageway at a first end of the heat sink and exit the passageway at a second end of the heat sink opposite the first end; and
mounting the support structure to the heat sink.

9. The method of claim 8, further comprising a plurality of plates positioned within the passageway and thermally coupled to the heat sink, each of the plurality of plates extending along the Z-direction.

10. The method of claim 8, further comprising a heat transfer enhancement device positioned within the heat sink and extending along the Z-direction.

11. The method of claim 10, wherein the heat transfer enhancement device is a heat pipe having a convective heat transfer medium positioned therein.

12. The method of claim 10, wherein the heat transfer enhancement device is a copper pipe.

13. The method of claim 8, further comprising positioning a heater between the support structure and the heat sink.

14. The method of claim 13, further comprising positioning a thermal barrier between the heat sink and the heater.

15. A CT system comprising:
a rotatable gantry having an opening for receiving an object to be scanned;
an x-ray tube having a focal spot from which x-rays emit; and
a detector assembly comprising one or more scintillator modules for receiving x-rays from the focal spot, the detector assembly comprising:
a plurality of detector modules, each detector module including a grid of pixelated scintillators, a photodiode having pixelations that correspond with the pixelated scintillators, and an electronics package for processing acquired X-ray data;
a support structure extending along a Z-direction of the CT system and having the plurality of detector modules positioned thereon; and
a heat sink extending along the Z-direction and having the support structure mounted thereon, the heat sink including a passageway passing therethrough and along the Z-direction, such that cooling air may pass into the passageway at a first end of the heat sink and exit the passageway at a second end of the heat sink opposite the first end.

16. The detector of claim 15, wherein the detector assembly further comprises a plurality of plates positioned within the passageway and thermally coupled to the heat sink, each of the plurality of plates extending along the Z-direction.

17. The detector of claim 15, wherein the detector assembly further comprises a heat transfer enhancement device positioned within the heat sink and extending along the Z-direction.

18. The detector of claim 17, wherein the heat transfer enhancement device is a heat pipe having a convective heat transfer medium positioned therein.

19. The detector of claim 15, further comprising a heater positioned between the support structure and the heat sink.

20. The detector assembly of claim 19, further comprising a thermal barrier positioned between the heat sink and the heater.

\* \* \* \* \*